US008361131B2

(12) United States Patent
Chin et al.

(10) Patent No.: US 8,361,131 B2
(45) Date of Patent: Jan. 29, 2013

(54) MULTI-COMPONENT K-WIRE

(75) Inventors: Kingsley R. Chin, West Palm Beach, FL (US); Christopher A. Chang, Beverly, MA (US)

(73) Assignee: Spinefrontier Inc, Beverly, MA (US)

( * ) Notice: Subject to any disclaimer, the term of this patent is extended or adjusted under 35 U.S.C. 154(b) by 1280 days.

(21) Appl. No.: 11/876,502

(22) Filed: Oct. 22, 2007

(65) Prior Publication Data

US 2008/0114363 A1     May 15, 2008

Related U.S. Application Data

(60) Provisional application No. 60/865,716, filed on Nov. 14, 2006.

(51) Int. Cl.
*A61B 17/86* (2006.01)
*A61F 2/08* (2006.01)
(52) U.S. Cl. ......................................................... 606/329
(58) Field of Classification Search .................... 606/53, 606/54, 55, 59, 263, 281, 300, 328, 329, 606/139–158; 403/150, 151, 162, 122–144; 16/387

See application file for complete search history.

(56) References Cited

U.S. PATENT DOCUMENTS

| | | | | | |
|---|---|---|---|---|---|
| 629,185 | A | * | 7/1899 | Arnold | 403/157 |
| 2,175,395 | A | * | 10/1939 | Hewel | 81/15.8 |
| 3,305,100 | A | * | 2/1967 | Barbee | 211/120 |
| 4,898,186 | A | * | 2/1990 | Ikada et al. | 606/62 |
| 5,261,918 | A | * | 11/1993 | Phillips et al. | 606/140 |
| 5,788,705 | A | * | 8/1998 | Huddleston et al. | 606/102 |
| 5,840,078 | A | * | 11/1998 | Yerys | 606/151 |
| 5,931,839 | A | | 8/1999 | Medoff | |
| 6,193,724 | B1 | * | 2/2001 | Chan | 606/102 |
| 7,044,951 | B2 | | 5/2006 | Medoff et al. | |
| 7,811,311 | B2 | * | 10/2010 | Markworth et al. | 606/278 |
| 7,905,924 | B2 | * | 3/2011 | White | 623/18.11 |

* cited by examiner

*Primary Examiner* — Anu Ramana
(74) *Attorney, Agent, or Firm* — AKC Patents LLC; Aliki K. Collins

(57) ABSTRACT

A surgical tool includes first and second K-wire components that are configured to pivot relative to each other and their relative position can be securely locked. The locking mechanism may be a sleeve, a retention ring or a collet.

17 Claims, 6 Drawing Sheets

MULTI-COMPONENT K-WIRE

CROSS REFERENCE TO RELATED CO-PENDING APPLICATIONS

This application claims the benefit of U.S. provisional application Ser. No. 60/865,716 filed Nov. 14, 2006 and entitled "SYSTEM AND METHOD FOR A PIVOTING K-WIRE", the contents of which are expressly incorporated herein by reference.

FIELD OF THE INVENTION

The present invention relates to system and method for a multi-component K-wire, and in particular for a multi-component K-wire comprising components pivoting relative to each other.

BACKGROUND OF THE INVENTION

A Kirschner wire (also called a K-wire) is a thin, rigid wire that can be used to stabilize bone fragments in orthopedics and other types of medical and veterinary surgery. Kirschner wires were introduced in surgical procedures by Martin Kirschner in 1909. They are sterilized, sharpened, smooth stainless steel pins and have different sizes. Typical K-wire diameters range from 0.7 millimeters to 1.6 millimeters. Either one or both wire ends are sharpened to a point. Point styles include trocar or diamond points. K-wires can be drilled through the bone to hold bone fragments in place. They are placed percutaneously (through the skin), thus avoiding open surgery in some cases. In other cases, K-wires are used after surgery to hold bone fragments in place. In some cases K-wires include threads for threading into the bone.

In spine surgery K-wires are used as guide wires for the placement of spine fixation components, such as screws and pins. They are inserted either through an open surgical procedure or under fluoroscopic or X-ray observation and are removed after the insertion of the screws. In several instances it is desirable to move the guide K-wires out of line of sight without removing them from the bone locations.

SUMMARY OF THE INVENTION

In general, in one aspect, the invention features a surgical tool configured to be implanted into bone or tissue including a first K-wire component comprising a first sharpened tip end and a second end and a second K-wire component comprising a first sharpened tip end and a second end and the second ends of the first and second K-wire components are pivotally connected to each other.

Implementations of this aspect of the invention may include one or more of the following features. The second ends of the first and second K-wire components may be pivotally connected to each other via a pivot pin. In this case, the surgical tool may further include a tubular sleeve and the tubular sleeve is configured to slide over the pivot pin when the first and second K-wire components are inline with each other. The second ends of the first and second K-wire components may be pivotally connected to each other via a collet. In this case, the second end of the second K-wire component comprises a sphere and the sphere engages the collet and the second end of the first K-wire component comprises a concave surface dimensioned to sit over the sphere within the collet. Partial removal of the second end of the first K-wire component from the collet separates the concave surface from the sphere and allows the first K-wire component to pivot relative to the second K-wire component. Reinsertion of the previously partially removed second end of the first K-wire component into the collet causes the concave surface to move onto and contact the sphere and thereby prevents the first K-wire component to pivot relative to the second K-wire component. The second ends of the first and second K-wire components may be pivotally connected to each other via a retention ring. In this case the second end of the second K-wire component comprises a sphere and the sphere engages a spherical groove formed within the second end of the first K-wire and the retention ring prevents disengagement of the sphere from the spherical groove while allowing pivoting motion of the first K-wire component relative to the second K-wire component. The surgical tool may be used as guidance tool for implantation of devices into bone or tissue. The devices may be implanted over or around the surgical tool. The surgical tool may be used as fixation tool for bone or tissue. The surgical tool may be implanted percutaneously into bone or tissue. The K-wire components may comprise one of metal, stainless steel, titanium, gold, silver, nickel, alloys thereof, ceramic, bone, PEEK, plastic, polymer, composites, absorbable material, metal matrix material, nitinol or other memory shape alloys or combinations thereof. The K-wire components may comprise flexible or rigid materials. The K-wire components may have adjustable lengths. The surgical tool may further include additional K-wire components.

In general in another aspect the invention features a method for implanting devices into bone or tissue including first providing a surgical guidance tool comprising a first K-wire component comprising a first sharpened tip end and a second end, a second K-wire component comprising a first sharpened tip end and a second end and wherein the second ends of the first and second K-wire components are pivotally connected to each other. Next, inserting the first sharpened tip end of the first K-wire component into a first location of a bone or a tissue. Next, inserting a device into the first location over the guidance tool wherein the second K-wire component is oriented inline with the first K-wire component, and the pivoting the second K-wire component away from the first K-wire component.

In general in another aspect the invention features a method for fixing bone or tissue including first providing a surgical tool comprising a first K-wire component comprising a first sharpened tip end and a second end, a second K-wire component comprising a first sharpened tip end and a second end and wherein the second ends of the first and second K-wire components are pivotally connected to each other. Next, inserting the first sharpened tip end of the first K-wire component into a first location of a bone or a tissue, and the pivoting the second K-wire component away from the first K-wire component.

Among the advantages of this invention may be one or more of the following. The pivoting K-wire components provide a solution to the problem of the K-wires obstructing or complicating the view during surgery. The K-wire components can be repeatable pivoted out of line of sight and back.

BRIEF DESCRIPTION OF THE DRAWINGS

Referring to the figures, wherein like numerals represent like parts throughout the several views.

DETAILED DESCRIPTION OF THE INVENTION

The present invention relates to a K-wire that comprises at least two components and the two components are moveable relative to each other. In particular, the two components may pivot relative to each other via a pivoting mechanism. Pivoting of the two components may also be selectively prevented by locking the two components in linear position or at an angle relative to each other via a locking mechanism. In one example, the locking mechanism is a sleeve (shown in FIG. 1), a retention ring (shown in FIG. 5) or a collet (shown in FIG. 3).

Figure 1:
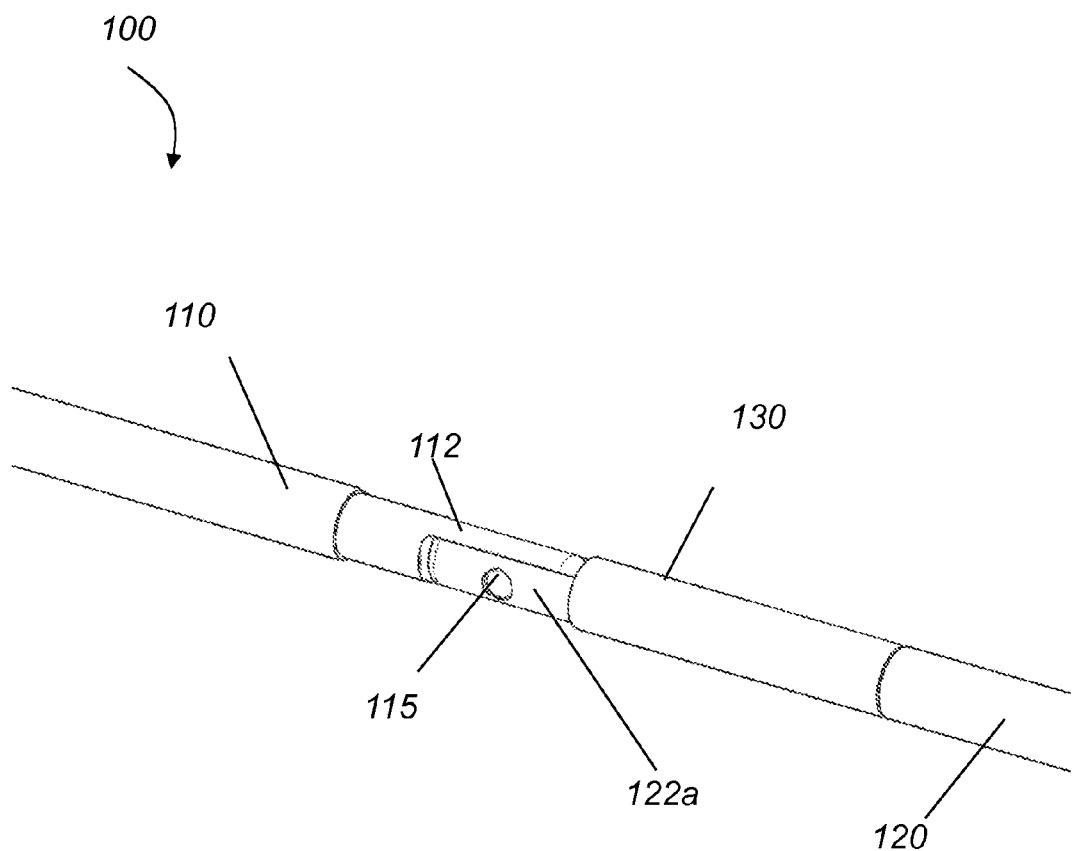
FIG. 1 is a perspective view of a first embodiment of a two component K-wire.

Referring to FIG. 1, a two component K-wire includes a first wire component 110 and a second wire component 120 pivotally connected to each other at pivot point 115. End 112 of wire component 110 is inserted in the gap between two end protrusions 122a, 122b of wire component 120 and pivot pin 115 is inserted through aligned holes formed in protrusions 122a, 122b and end 112, to pivotally connect wire components 110 and 120. A sleeve 130 is configured to slide over the pivoting connection between the wire components to prevent pivoting of the two wire components, when pivoting is not desired. Wire component 120 includes a portion 121 with a smaller diameter that wire component 120, over which sleeve 130 can slide.

Figure 2A:
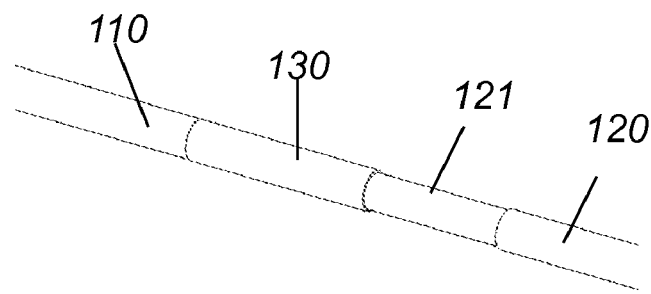
FIG. 2A-FIG. 2C depict the pivoting and locking mechanisms of the two components of the K-wire of FIG. 1.
Figure 2B:
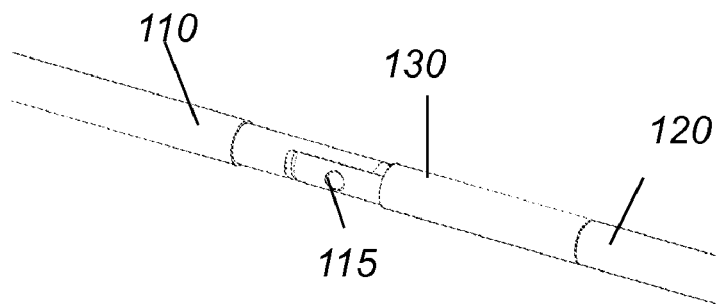
Figure 2C:
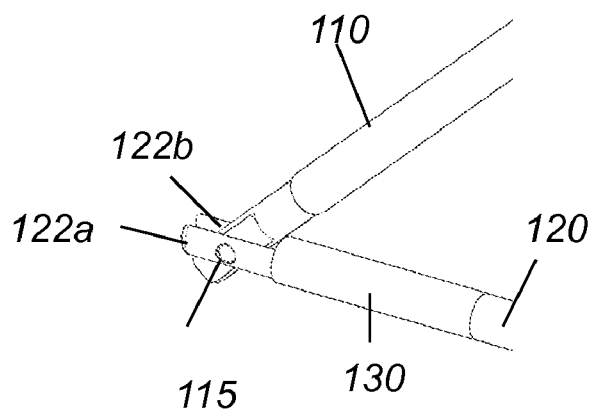

In operation, the two component K-wire 100 with the sleeve 130 over the pivoting connection, as shown in FIG. 2A, is inserted in the desired bone location with a pin gun or a high speed drill-type apparatus. When the K-wire is desired to be moved out of the line of sight sleeve 130 is moved away from the pivoting area (shown in FIG. 2B) by sliding it over portion 121, thereby allowing wire component 110 to be pivoted away from the linear direction of wire component 120 and to be placed at an angle relative to wire component 120, as shown in FIG. 2C.

Figure 3:
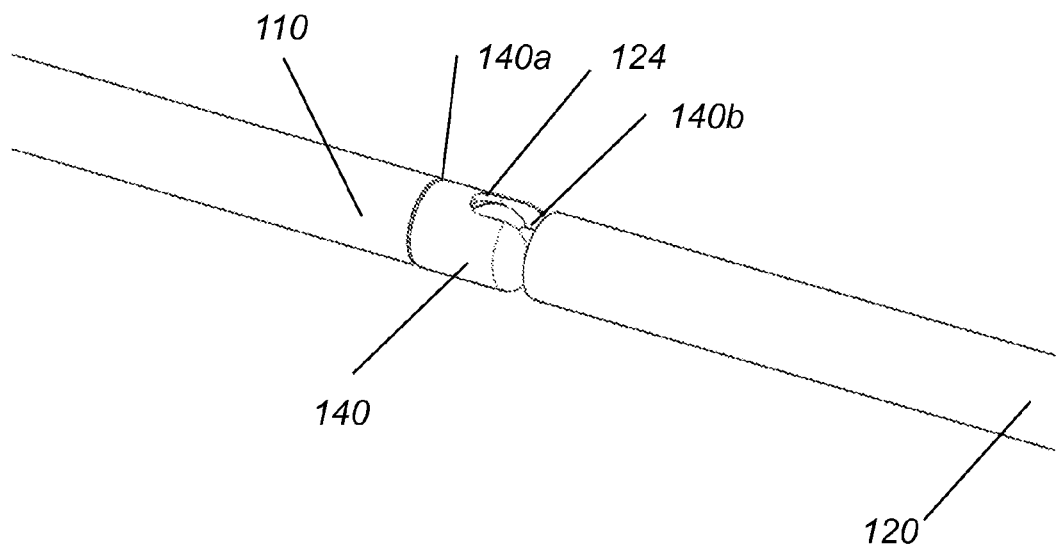
FIG. 3 is a perspective view of a second embodiment of a two component K-wire.

Referring to FIG. 3, in another embodiment, a two component K-wire includes a first wire component 110 and a second wire component 120 pivotally connected to each other via a collet 140. End 114 of wire component 110 includes threads 113 designed to engage inner threads in the tubular end 140a of collet 140. End 124 of wire component 120 is a sphere and is captured in a slot 140b of collet 140. Slot 140b is opposite to end 140a of collet 140. End 114 of wire component 110 has a semi-spherical shaped end surface 111 dimensioned to fit over sphere 124. When pivoting of wire components 110, 120 relative to each other is not desired, wire components 110, 120 are locked in line by inserting spherical end 124 of component 120 into the slot 140b and then screwing end 114 of component 110 in the opposite end 140a of collet 140 so that end surface 111 is pressed against the spherical end 124, as shown in FIG. 4A.

Figure 4A:
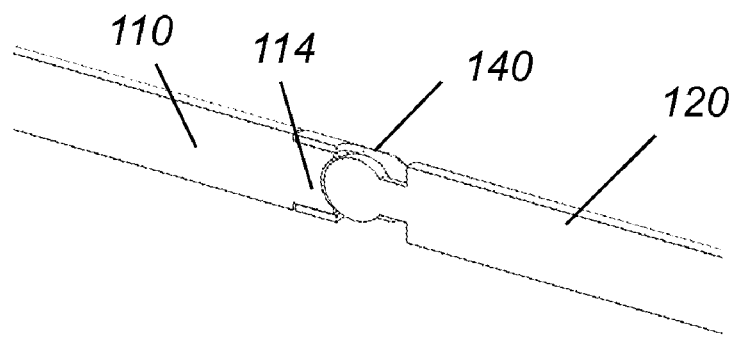
FIG. 4A-FIG. 4C depict cross-sectional views of the pivoting and locking mechanisms of the two components of the K-wire of FIG. 3.
Figure 4B:
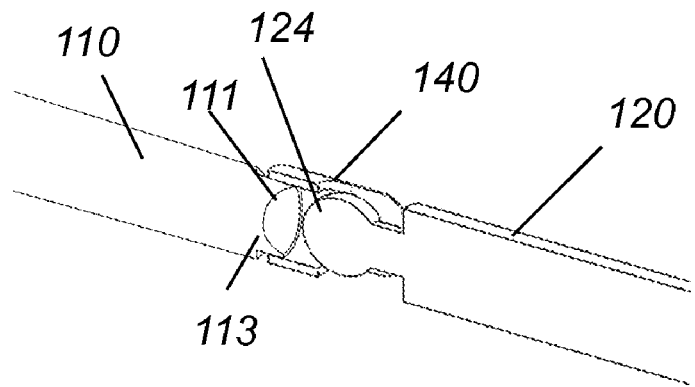

In operation, the two component K-wire 100 in the locked position, as shown in FIG. 4A, is inserted in the desired bone location with a pin gun or a high speed drill-type apparatus. When the K-wire is desired to be moved out of the line of sight, end 114 of wire component 110 is partially unscrewed from end 140a of collet 140 thereby moving surface 111 away from spherical end 124 of wire component 120, as shown in FIG. 4B.

Figure 4C:
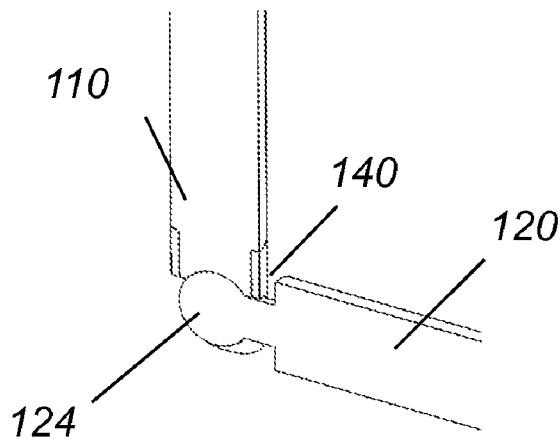

This provides enough space within slot 124 for pivoting wire component 110 around the sphere 124, as shown in FIG. 4C. Finally, wire component 110 is screwed back into end 140a to secure the new position of wire component 110 relative to wire component 120. In this embodiment, wire component 110 may be totally unscrewed from collet 140 and removed from wire component 120 and then reattached to wire component 120, if it is desired. In other embodiments, end 114 is designed to slide in collet end 140a and snap-in or snap-out of place over sphere 124.

Figure 5:
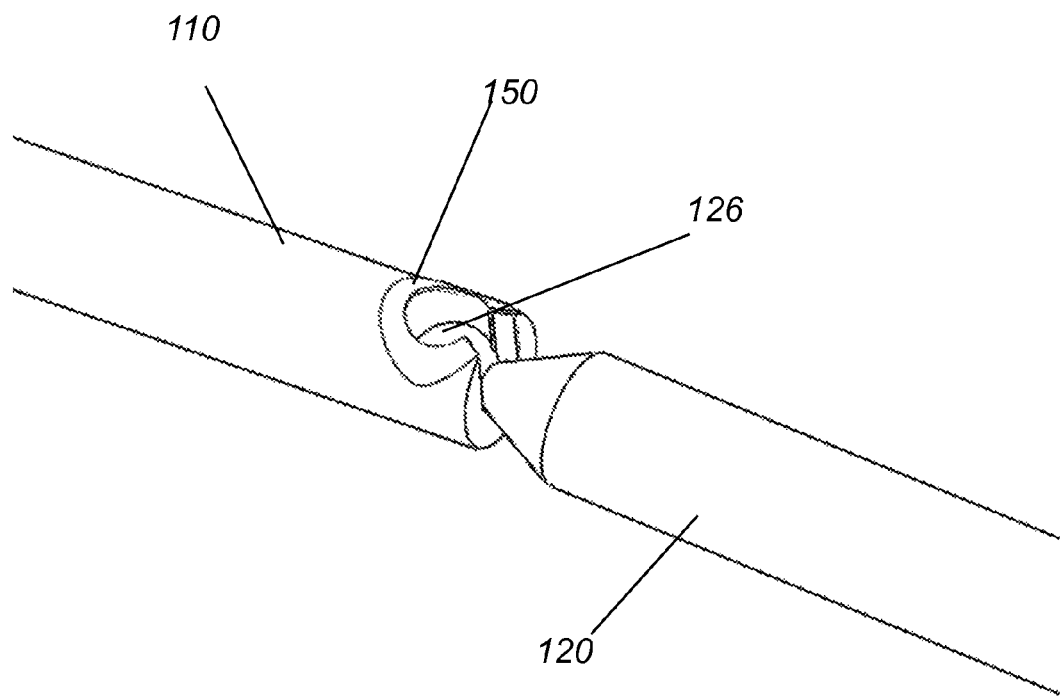
FIG. 5 is a perspective view of a third embodiment of a two component K-wire.
Figure 6A:
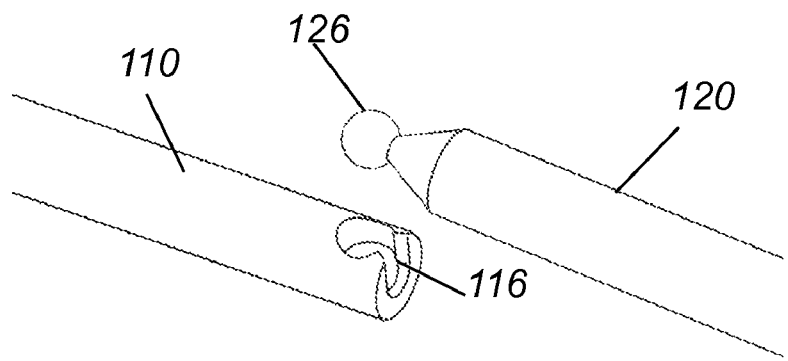
FIG. 6A-FIG. 6C depict the pivoting and locking mechanisms of the two components of the K-wire of FIG. 5.
Figure 6B:
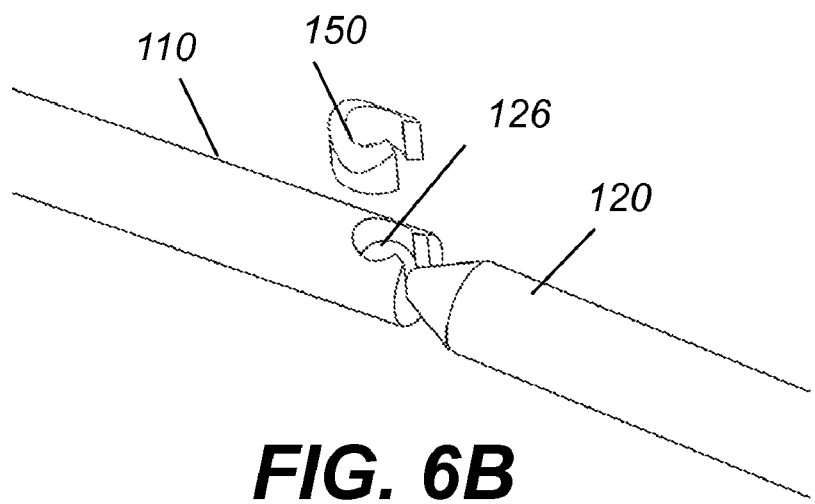
Figure 6C:
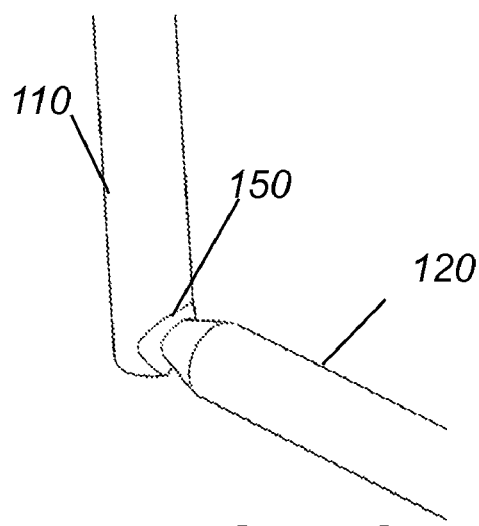

Referring to FIG. 5, in another embodiment, a two component K-wire includes a first wire component 110 and a second wire component 120 pivotally connected to each other via a pivoting sphere 126. Pivoting sphere 126 is formed at the end of wire component 120 and is dimensioned to fit and pivot within a spherical opening 116 formed in the end of wire component 110, shown in FIG. 6A. After placing sphere 126 into opening 116, a retention ring 150 is snapped into the opening 116 on top of the sphere to prevent disengagement of the two wire components (shown in FIG. 6B), while allowing wire component 110 to pivot around the pivot sphere 126, shown in FIG. 6C.

Other embodiments are within the scope of the following claims. The K-wire components may be made of materials including metal, ceramic, bone, PEEK, plastic, stainless steel, titanium, gold, silver, nickel, alloys thereof, polymer, composites, absorbable material, metal matrix material, nitinol or other memory shape alloys or combinations thereof. The memory shape K-wire component may be bend via a clamp, a spring loaded clamp or a weight. The pivoting K-wire components may be used for fixing bones, tissues or organs. In particular, the pivoting K-wire components may be used in spine fixation procedures. In other applications the pivoting K-wires may be used as cardiac catheters, brain catheters or stents, urethral catheters or stents. When used as guide wires, the K-wire components may be completely or partially surrounded by tools or cannulas placed over them or around them. The pivoting mechanisms may be integral with the K-wire components or removably attached to the K-wire components. The K-wire components may have adjustable lengths. The length adjusting mechanism may be a collapsible antenna mechanism.

Several embodiments of the present invention have been described. Nevertheless, it will be understood that various modifications may be made without departing from the spirit and scope of the invention. Accordingly, other embodiments are within the scope of the following claims.

What is claimed is:

1. A surgical tool configured to be implanted into bone or tissue comprising:
   a first K-wire component comprising a first sharpened tip end and a second end;
   a second K-wire component comprising a first sharpened tip end and a second end;
   a tubular sleeve;
   wherein a surface of the second end of the first K-wire component overlaps a surface of the second end of the second K-wire component and wherein said second ends of said first and second K-wire components are pivotally connected to each other via a pivot pin; and
   wherein said tubular sleeve is configured to slide over said pivot pin when said first and second K-wire components are coaxial with each other such that a longitudinal axis of the first K-wire component and a longitudinal axis of the second K-wire component are colinear.

2. The surgical tool of claim 1 wherein said tool is used as guidance tool for implantation of devices into bone or tissue.

3. The surgical tool of claim 2 wherein said devices are implanted over said surgical tool.

4. The surgical tool of claim 2 wherein said devices are implanted around said surgical tool.

5. The surgical tool of claim 1 wherein said tool is used as fixation tool for bone or tissue.

6. The surgical tool of claim 1 wherein said tool is implanted percutaneously into bone or tissue.

7. The surgical tool of claim 1 wherein said K-wire components comprise one of metal, stainless steel, titanium, gold, silver, nickel, alloys thereof, ceramic, bone, PEEK, plastic, polymer, composites, absorbable material, metal matrix material, nitinol or other memory shape alloys or combinations thereof.

8. The surgical tool of claim 1 wherein said K-wire components comprise flexible materials.

9. The surgical tool of claim 1 wherein said K-wire components comprise rigid materials.

10. A surgical tool configured to be implanted into bone or tissue comprising:
    a first K-wire component comprising a first sharpened tip end and a second end;
    a second K-wire component comprising a first sharpened tip end and a second end; and wherein a surface of the second end of the first K-wire component overlaps a surface of the second end of the second K-wire component and wherein said second ends of said first and second K-wire components are pivotally connected to each other via a retention ring; and
    wherein said second end of said second K-wire component comprises a sphere and said sphere engages a spherical groove formed within said second end of said first K-wire and wherein said retention ring presents disengagement of said sphere from said spherical groove while allowing pivoting motion of said first K-wire component relative to said second K-wire component.

11. A surgical tool configured to be implanted into bone or tissue comprising:
    a first K-wire component comprising a first sharpened tip end and a second end;
    a second K-wire component comprising a first sharpened tip end and a second end; and wherein said second ends of said first and second K-wire components are pivotally connected to each other via a collet and wherein said collet comprises a threaded tubular first end and a slotted second end.

12. The surgical tool of claim 11 wherein said second end of said second K-wire component comprises a sphere and said sphere engages said slotted second end of said collet.

13. The surgical tool of claim 12 wherein said second end of said first K-wire component comprises outer threads configured to engage the threaded first end of said collet and wherein said second end of said first K-wire component further comprises a concave surface dimensioned to sit over said sphere within said collet.

14. The surgical tool of claim 13 wherein partial removal of said second end of said first K-wire component from said collet separates said concave surface from said sphere and allows said first K-wire component to pivot relative to said second K-wire component within the slot of said second end of said collet.

15. The surgical tool of claim 14 wherein reinsertion of said previously partially removed second end of said first K-wire component into said collet causes said concave surface to be pressed against said sphere and thereby to lock said first K-wire component relative to said second K-wire component.

16. A method for implanting devices into bone or tissue comprising:
    providing a surgical guidance tool comprising a first K-wire component comprising a first sharpened tip end and a second end, a second K-wire component comprising a first sharpened tip end and a second end and wherein said second ends of said first and second K-wire components are pivotally connected to each other;
    inserting said first sharpened tip end of said first K-wire component into a first location of a bone or a tissue;
    inserting a device into said first location over said guidance tool wherein said second K-wire component is oriented coaxially with said first K-wire component; and
    pivoting said second K-wire component away from said first K-wire component.

17. A method for fixing bone or tissue comprising:
    providing a surgical tool comprising a first K-wire component comprising a first sharpened tip end and a second end, a second K-wire component comprising a first sharpened tip end and a second end and wherein a surface of the second end of the first K-wire component overlaps a surface of the second end of the second K-wire component and wherein said second ends of said first and second K-wire components are pivotally connected to each other via a pivot pin;
    inserting said first sharpened tip end of said first K-wire component into a first location of a bone or a tissue; and
    pivoting said second K-wire component away from said first K-wire component.

\* \* \* \* \*